US012332616B2

(12) United States Patent
Kawashima et al.

(10) Patent No.: US 12,332,616 B2
(45) Date of Patent: Jun. 17, 2025

(54) FLUID BALANCE MANAGEMENT SYSTEM, PREDICTION DEVICE, LEARNED MODEL GENERATION DEVICE, AND LEARNED MODEL GENERATION METHOD

(71) Applicant: NIHON KOHDEN CORPORATION, Tokyo (JP)

(72) Inventors: Takuya Kawashima, Tokorozawa (JP); Wataru Matsuzawa, Tokorozawa (JP); Hiroto Sano, Tokorozawa (JP); Katsuyoshi Suzuki, Tokorozawa (JP); Yoshihiro Takayanagi, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 479 days.

(21) Appl. No.: 17/947,886

(22) Filed: Sep. 19, 2022

(65) Prior Publication Data
US 2023/0094927 A1    Mar. 30, 2023

(30) Foreign Application Priority Data
Sep. 30, 2021    (JP) .................................. 2021-160976

(51) Int. Cl.
*G05B 13/04*    (2006.01)
*G05B 13/02*    (2006.01)

(52) U.S. Cl.
CPC ....... *G05B 13/048* (2013.01); *G05B 13/0265* (2013.01)

(58) Field of Classification Search
CPC .. G05B 15/02; G05B 13/048; G05B 13/0265; A61B 5/00
See application file for complete search history.

(56) References Cited

U.S. PATENT DOCUMENTS

| 5,393,938 | A  | * | 2/1995 | Bumbalough | ....... | G01G 19/445 |
| | | | | | | 177/144 |
| 2007/0118054 | A1 | * | 5/2007 | Pinhas | .................. | G16H 40/67 |
| | | | | | | 600/587 |
| 2007/0136102 | A1 | | 6/2007 | Rodgers | | |

(Continued)

FOREIGN PATENT DOCUMENTS

| CA | 2668602 | A1 | * | 5/2007 | ............... | A61B 5/01 |
| CA | 3140320 | A1 | * | 12/2020 | ............. | A61B 5/002 |

(Continued)

OTHER PUBLICATIONS

Communication dated Jan. 27, 2023 issued by the European Patent Office in application No. 22196334.1.

(Continued)

*Primary Examiner* — Ronald D Hartman, Jr.
(74) *Attorney, Agent, or Firm* — Sughrue Mion, PLLC

(57) ABSTRACT

A fluid balance management system includes: a detection device configured to output a detection signal corresponding to a load applied to a bed in which a subject is present; a prediction device configured to acquire load variation information indicating a variation over time of the load based on the detection signal, and predict an event that causes variation in fluid balance of the subject from the load variation information; and an output device configured to output prediction information corresponding to a prediction result of the event.

11 Claims, 4 Drawing Sheets

(56) References Cited

U.S. PATENT DOCUMENTS

| | | | | |
|---|---|---|---|---|
| 2008/0077020 A1* | 3/2008 | Young | ................ | A61B 5/746 |
| | | | | 73/726 |
| 2008/0115592 A1* | 5/2008 | Wang | ................ | G01G 5/04 |
| | | | | 73/862.581 |
| 2019/0053761 A1* | 2/2019 | Young | ................ | A61B 5/1102 |
| 2021/0287791 A1* | 9/2021 | Bhai | ................ | A61B 5/1127 |
| 2023/0094927 A1* | 3/2023 | Kawashima | ................ | G16H 20/60 |
| | | | | 700/281 |
| 2024/0119820 A1* | 4/2024 | Williams | ................ | G06N 3/08 |

FOREIGN PATENT DOCUMENTS

| | | | | | |
|---|---|---|---|---|---|
| EP | 3878362 A1 | | 9/2021 | | |
| FR | 2472936 A1 | * | 7/1981 | ......... | A61M 1/1639 |
| JP | 2001-337998 A | | 12/2001 | | |
| JP | 2004271368 A | * | 9/2004 | | |
| JP | 2018-19763 A | | 2/2018 | | |
| JP | 2020-80019 A | | 5/2020 | | |
| JP | 2020-154735 A | | 9/2020 | | |
| WO | 2017085583 A1 | | 5/2017 | | |
| WO | WO-2018219809 A1 | * | 12/2018 | ......... | A61B 5/0002 |

OTHER PUBLICATIONS

Communication issued on Dec. 24, 2024 from the Japan Patent Office for Japanese Patent Application No. 2021-160976.

* cited by examiner

FLUID BALANCE MANAGEMENT SYSTEM, PREDICTION DEVICE, LEARNED MODEL GENERATION DEVICE, AND LEARNED MODEL GENERATION METHOD

CROSS-REFERENCE TO RELATED APPLICATIONS

This application is based on and claims priority under 35 USC 119 from Japanese Patent Application No. 2021-160976 filed on Sep. 30, 2021, the contents of which are incorporated herein by reference.

TECHNICAL FIELD

The presently disclosed subject matter relates to a system that manages fluid balance information based on fluid intake and excretion of a subject. The presently disclosed subject matter also relates to a prediction device that predicts an event that causes variation in fluid balance of a subject, and to a non-transitory computer-readable storage medium storing a computer program that can be executed by a processor mounted in the prediction device. The presently disclosed subject matter also relates to a generation device that generates a learned model used for prediction by the prediction device, and a non-transitory computer-readable storage medium storing a computer program that can be executed by a processor mounted in the generation device. The presently disclosed subject matter also relates to a method for generating a learned model.

BACKGROUND ART

In a medical facility or the like, body weight measurement of a patient as an example for a subject is performed at a frequency of once per day to once per several days. The management of fluid balance is performed by comparing weight increase or decrease due to fluid intake and/or urine discharge by the patient in a period from the previous body weight measurement with body weight variation of the patient in the period.

Japanese Patent Application Publication No. 2001-337998 discloses a system for electronically managing fluid balance information.

An object of the presently disclosed subject matter is to enhance manageability of fluid balance information of a subject.

SUMMARY

A first aspect of the presently disclosed subject matter relates to a fluid balance management system including: a detection device configured to output a detection signal corresponding to a load applied to a bed in which a subject is present; a prediction device configured to acquire load variation information indicating a variation over time of the load based on the detection signal, and predict an event that causes variation in fluid balance of the subject from the load variation information; and an output device configured to output prediction information corresponding to a prediction result of the event.

A second aspect of the presently disclosed subject matter relates to a prediction device including: an interface configured to receive load variation information indicating a variation over time of a load applied to a bed in which a subject is present, the variation over time being acquired based on a detection signal corresponding to the load; and one or more processors configured to predict an event that causes variation in fluid balance of the subject from the load variation information, and output information corresponding to a prediction result of the event to an output device A third aspect of the presently disclosed subject matter relates to a non-transitory computer-readable storage medium storing a computer program executable by one or more processors mounted in a prediction device. When the computer program is executed, the prediction device: receives load variation information indicating a variation over time of a load applied to a bed in which a subject is present, the variation over time being acquired based on a detection signal corresponding to the load; predicts an event that causes variation in fluid balance of the subject from the load variation information; and outputs information corresponding to a prediction result of the event to an output device.

According to the configuration according to each of the first to third aspects described above, the weight variation associated with the variation in fluid balance of the subject during being away from bed is reflected in the variation in the load applied to the bed when the subject returns to the bed. Since the event that causes the variation in fluid balance is predicted based on the variation, it is possible to automate the management of the fluid balance while the subject is in bed. As a result, it is possible to easily perform management inclusive of the fluid balance during being away from bed, which has not been managed so far, and thus it is possible to improve the management of the fluid balance information of the subject inclusive of not only while the subject is in bed but also away from bed. In addition, it is possible to automate complementary record of the fluid balance during being away from bed, which has been generally performed manually so far, and thus it is possible to reduce the burden on the user.

A fourth aspect of the presently disclosed subject matter relates to a learned model generation device including: an interface configured to receive, as learning data, a combination of load variation information indicating a variation over time of a load applied to a bed in which a subject is present, the variation over time being acquired based on a detection signal corresponding to the load, and event information indicating an event that causes variation in fluid balance of the subject associated with the variation over time: and one or more processors configured to execute machine learning based on the learning data, thereby generating a learned model for predicting the event from the load variation information.

A fifth aspect of the presently disclosed subject matter relates to a non-transitory computer-readable storage medium storing a computer program executable by one or more processors mounted in a learned model generation device. When the computer program is executed, the learned model generation device: receives, as learning data, a combination of load variation information indicating a variation over time of a load applied to a bed in which a subject is present, the variation over time being acquired based on a detection signal corresponding to the load, and event information indicating an event that causes variation in fluid balance of the subject associated with the variation over time; and executes machine learning based on the learning data, thereby generating a learned model for predicting the event from the load variation information.

A sixth aspect of the presently disclosed subject matter relates to a learned model generation method including: receiving, as learning data, a combination of load variation information indicating a variation over time of a load applied to a bed in which a subject is present, the variation over time being acquired based on a detection signal corresponding to the load, and event information indicating an event that causes variation in fluid balance of the subject associated with the variation over time; and executing machine learning based on the learning data, thereby generating a learned model for predicting the event from the load variation information.

According to the configuration according to each of the fourth to sixth aspects described above, it is possible to provide a learned model capable of not only reducing the burden related to prior design of explicit rules for prediction of the event that causes variation in fluid balance or excretion, which is performed by the prediction device according to each of the first to third aspects, but also capable of enhancing generalization performance of the prediction device.

BRIEF DESCRIPTION OF DRAWINGS

An exemplary embodiment of the present invention will be described in detail based on the following figures, wherein.

DESCRIPTION OF EMBODIMENTS

An example for an embodiment will be described in detail below with reference to the accompanying drawings.

Figure 1:
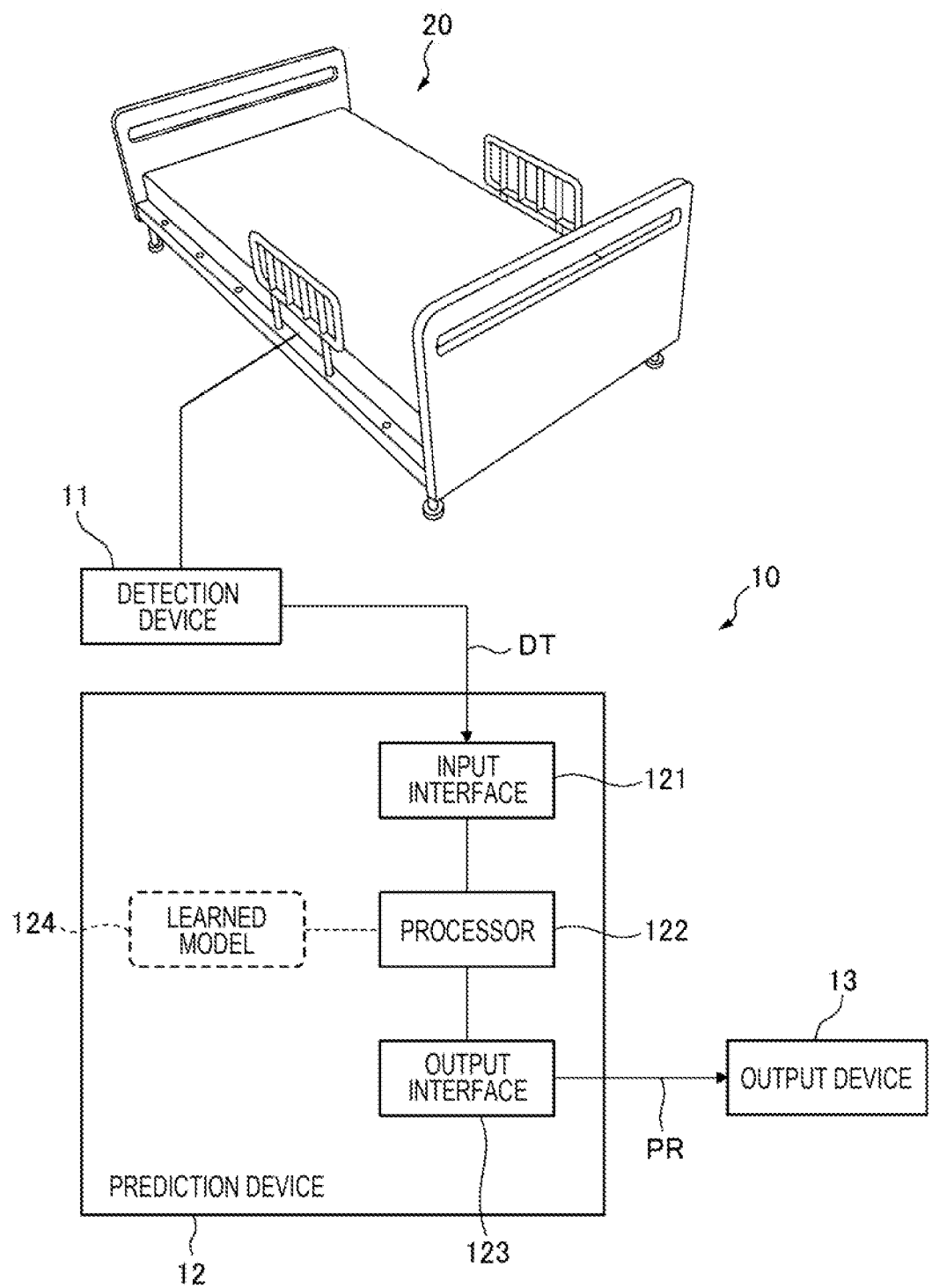
FIG. 1 illustrates an example of a functional configuration of a fluid balance management system according to an embodiment.

FIG. 1 illustrates a functional configuration of a fluid balance management system 10 (hereinafter, abbreviated as a management system 10) according to an embodiment. The management system 10 is configured to manage fluid balance information based on fluid intake and excretion of a subject. As an example, the fluid is water. But the fluid is not limited to water.

The management system 10 can include a detection device 11. The detection device 11 is configured to detect a load applied to a bed 20 in which the subject is present and to output a detection signal DT corresponding to the load. That is, the detection signal DT corresponds to the body weight of the subject present in the bed 20.

The output of the detection signal DT may be performed continuously in time or may be performed intermittently every time a predetermined time period elapses. The output detection signal DT may be either an analog signal or a digital signal.

The detection device 11 may take an appropriate aspect. As an example, the detection device 11 may be configured to include a load meter (so-called bed scale) disposed between each leg of the bed 20 and the floor. In this case, the detection device 11 generates the detection signal DT based on the load detected by each load meter. As another example, the detection device may be a load sensor embedded in a mattress or a leg of the bed 20. In this case, the detection device 11 generates the detection signal DT based on the load detected by the load sensor.

The management system 10 can include a prediction device 12. The prediction device 12 is configured to acquire load variation information indicating a variation over time of the load applied to the bed 20 based on the detection signal DT, and predict an event that causes variation in fluid balance of the subject from the load variation information. Examples of the event include eating, drinking, excretion (including nocturia), insensible fluid loss, and the like.

Specifically, the prediction device 12 can include an input interface 121. The input interface 121 is configured to receive the detection signal DT output from the detection device 11. In a case where the detection signal DT is an analog signal, the input interface 121 may include an appropriate conversion circuit including an A/D converter.

The prediction device 12 can include a processor 122. The processor 122 is configured to acquire the load variation information LV illustrated in FIG. 2 based on the detection signal DT received by the input interface 121. The horizontal axis represents the elapse of time. The vertical axis represents the load applied to the bed 20. The frequently appearing periods in which the load disappears indicate a situation in which the subject leaves the bed 20.

The processor 122 is configured to predict an event that causes variation in fluid balance of the subject based on the load variation information LV. Some examples for the prediction are given below.

In a period T, without variation corresponding to the patient leaving the bed, the load decreases gradually. In a case where such a variation is confirmed, the processor 122 predicts insensible fluid loss as an event that causes variation in fluid balance.

At a time point t1, the load shows a variation (namely, change) corresponding to the patient leaving the bed, and then shows a significant increase. In a case where such a variation is confirmed, the processor 122 predicts eating as an event that causes variation in fluid balance.

At a time point t2, the load shows a variation corresponding to the patient leaving the bed, and then shows a significant decrease. In a case where such a variation is confirmed, the processor 122 predicts excretion as an event that causes variation in fluid balance.

The prediction device 12 can include an output interface 123. The processor 122 is configured to output prediction information PR corresponding to the prediction result from the output interface 123. The prediction information PR is configured to include a predicted event and a time at which the event occurred. The prediction information PR may be output in the form of analog data, or may be output in the form of digital data. When the prediction information PR is provided in the form of analog data, the output interface 123 includes an appropriate conversion circuit including a D/A converter.

The management system 10 can include an output device 13. The output device 13 may be a stationary device installed on the bed 20, or may be a mobile device that can be carried by a user. The prediction information PR output from the output interface 123 is transmitted to the output device 13. The prediction information PR may be transmitted through wired communication or wireless communication. The output device 13 is configured to output a prediction result by the prediction device 12 based on the prediction information PR. The output from the output device 13 may take an appropriate aspect involving at least one of presenting the prediction result to a user or recording the prediction information PR in a storage device (not shown).

According to such a configuration, the weight variation associated with the variation in fluid balance of the subject during being away from the bed 20 is reflected in the variation in the load applied to the bed when the subject returns to the bed 20. Since the event that causes the variation in fluid balance is predicted based on the variation, it is possible to automate the management of the fluid balance during being in bed. As a result, it is possible to easily perform management inclusive of the fluid balance during being away from bed, which has not been managed so far, and thus it is possible to improve the management of the fluid balance information of the subject inclusive of not only during being in bed but also during being away from bed. In addition, it is possible to automate complementary record of the fluid balance during being away from bed, which has been generally performed manually so far, and thus it is possible to reduce the burden on the user.

Figure 3:
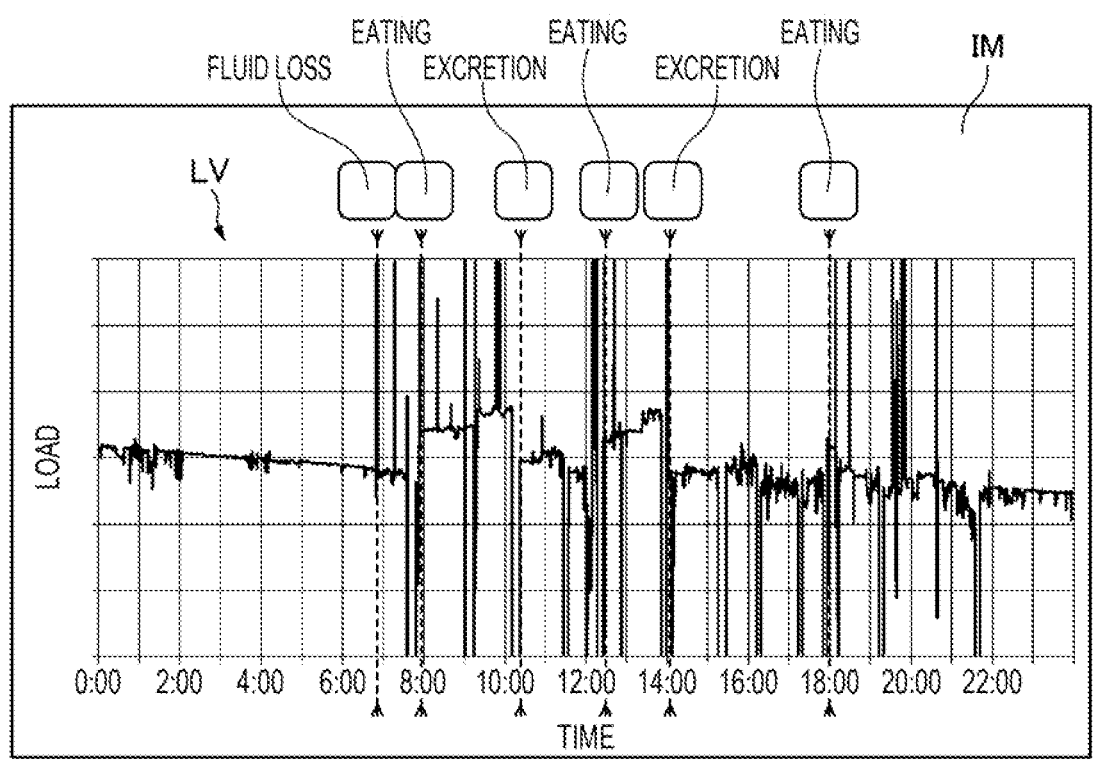
FIG. 3 illustrates an example for information output by an output device of FIG. 1.

In order to enhance the visibility of the managed fluid balance information, the output device 13 may be configured to output an image IM exemplified in FIG. 3. The image IM represents an index corresponding to the prediction result by the prediction device 12 together with the load variation information LV. In this example, the index can include a marker indicating a time point predicted as occurrence of an event, and an icon indicating the predicted event. In this example, the icon can include characters indicating an event. In addition to or instead of characters, the event may be specified by a color, a symbol, a figure, or the like.

In addition to or instead of the information corresponding to the prediction information PR, the output device 13 may output body weight variation information indicating a weight variation of the subject associated with occurrence of the event related to the prediction. Specifically, the processor 122 of the prediction device 12 specifies, as the load variation information LV, variation generated in the load applied to the bed 20 before and after the occurrence time point of the event included in the prediction information PR. As described above, since the load applied to the bed 20 corresponds to the body weight of the subject, the variation of the load can be used as the body weight variation information.

According to such a configuration, since it is possible to automate the record of the weight variation caused by variation in fluid balance of the subject, it is possible to further reduce the burden on the user related to management of the fluid balance information.

As illustrated in FIG. 1, the prediction device 12 may include a learned model 124. The processor 122 may be configured to perform a process of inputting the load variation information LV to the learned model 124, thereby acquiring the prediction result of the event that causes the variation in fluid balance of the subject.

The learned model 124 is a prediction algorithm generated through machine learning by using a neural network to be described later. The learned model 124 is configured to output, as the prediction result, an event that causes variation in fluid balance of the subject, with the load variation information LV indicating the variation over time of the load applied to the bed 20 as an input.

Figure 4:
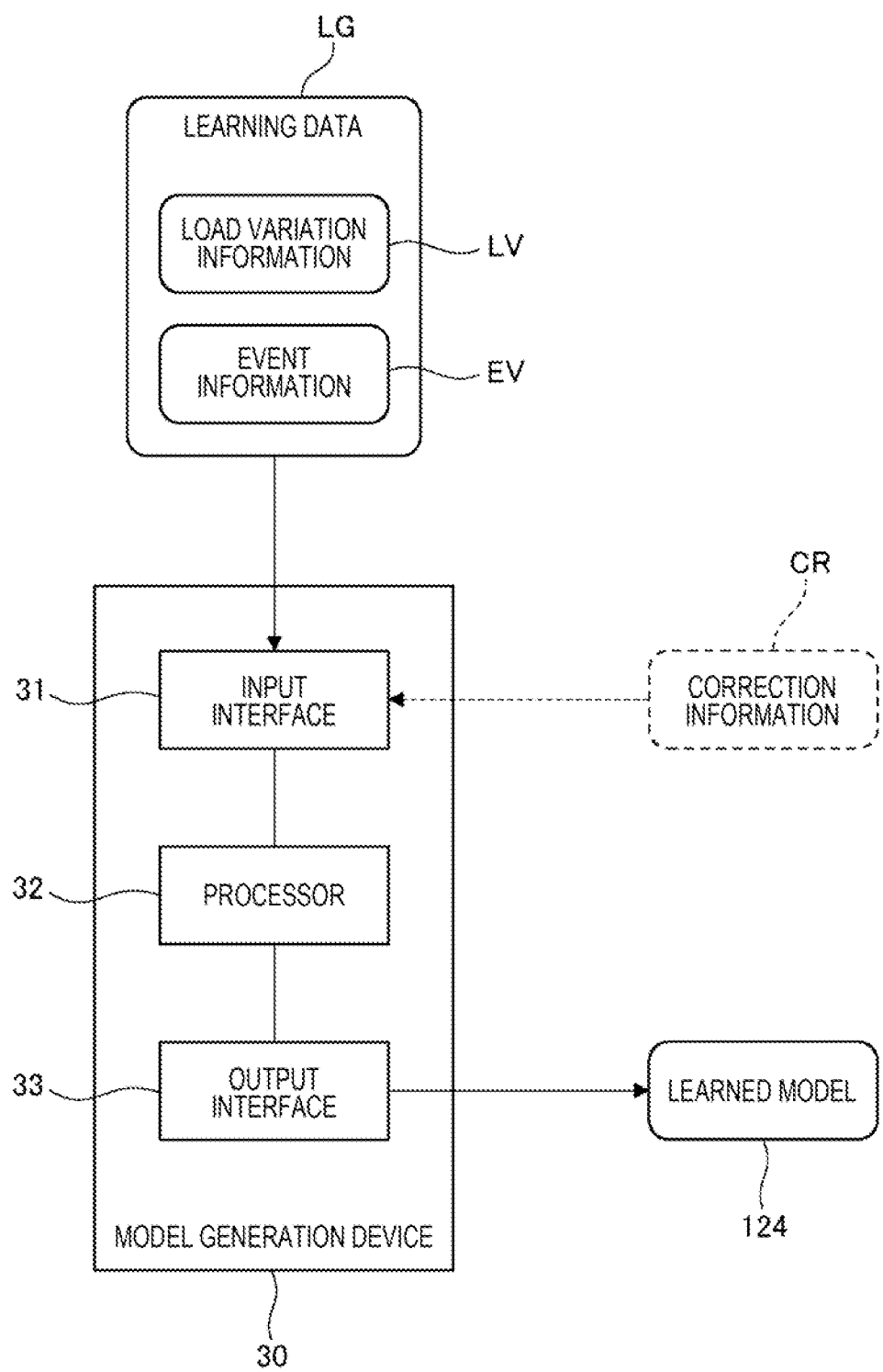
FIG. 4 illustrates an example of a functional configuration of a model generation device according to an embodiment.

The learned model 124 is generated by a model generation device 30 illustrated in FIG. 4. That is, the model generation device 30 is configured to generate the learned model 124 to be installed in the prediction device 12.

The model generation device 30 can include an input interface 31. The input interface 31 is configured to receive learning data LG. The learning data LG can include the load variation information LV acquired for a certain subject and the event information EV indicating an event that causes variation in fluid balance of the subject.

The model generation device 30 can include a processor 32. The processing unit 32 is configured to generate the learned model 124 by causing a neural network to perform learning using the learning data LG. As processing for causing the neural network to perform learning, a method related to supervised learning is used.

Specifically, the learning data LG is provided with training data for teaching the type of the load variation information LV to be acquired when variation in fluid balance occurs in the subject, based on the type of the event.

The learning data LG may include information such as temperature, humidity, time, and the like as the information related to the body weight variation of the subject.

The model generation device 30 can include an output interface 33. The output interface 33 is configured to output the learned model 124 generated by the processor 32 in a form that can be installed in the prediction device 12.

According to such a configuration, it is possible to not only reduce the burden related to prior design of explicit rules for prediction of the event that causes variation in fluid balance, which is performed by the prediction device 12, but also enhance generalization performance of the prediction device 12.

Figure 2:
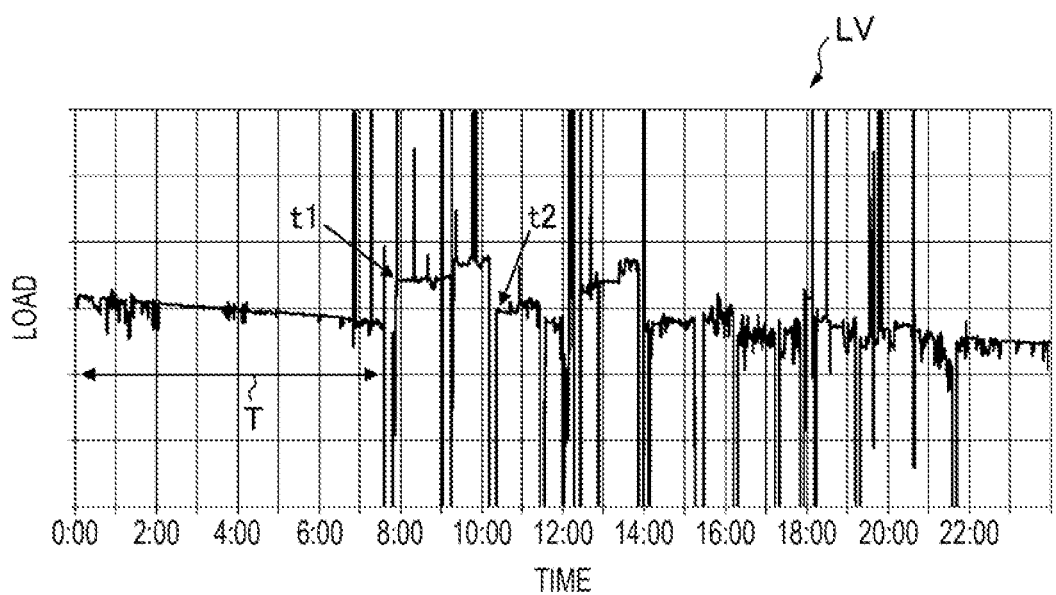
FIG. 2 illustrates an example of load variation information acquired by a prediction device of FIG. 1.

The learned model 124 may be configured to enable relearning. For example, in a case where the body weight variation of the subject occurring in the period T of FIG. 2 is caused by nocturia rather than insensible fluid loss, the prediction result displayed by the index illustrated in FIG. 3 is an error. In such a case, the prediction information PR may be corrected as necessary.

As illustrated in FIG. 4, correction information CR corresponding to the correction can be input to the input interface 31 of the model generation device 30. In this example, the correction information CR is provided as a combination of the load variation information LV subjected to incorrect prediction and the event information corresponding to "nocturia", which is a corrected event. The processor 32 of the model generation device 30 performs relearning of the learned model 124 to reflect the correction information CR. The timing of relearning can be set as appropriate.

The relearning of the learned model 124 may be configured to be executed by the processor 122 of the prediction device 12. In this case, the input interface 121 of the prediction device 12 is configured to receive the correction information CR.

According to such a configuration, it is possible to improve the prediction accuracy of the event that causes variation in fluid balance by the prediction device 12 based on the information acquired from the subject after the start of the operation of the management system 10.

The processor 122 of the prediction device 12 and the processor 32 of the model generation device 30 having the various functions described above may be each implemented by a general-purpose microprocessor that operates in cooperation with a general-purpose memory. Examples of the general-purpose microprocessor include a CPU, an MPU, and a GPU. Examples of the general-purpose memory include a ROM and a RAM. In this case, the ROM may store a computer program that executes the above-described processing. The ROM is an example for a non-transitory computer-readable medium storing the computer program. The general-purpose microprocessor specifies at least a part of programs stored in the ROM, loads the program into a RAM, and executes the above-described processing in cooperation with the RAM. The computer program may be pre-installed in the general-purpose memory, or may be downloaded from an external server via a communication network and be installed in the general-purpose memory. In this case, the external server is an example for a non-transitory computer-readable medium storing the computer program.

The processor 122 of the prediction device 12 and the processor 32 of the model generation device 30 having the various functions described above may be each implemented by a dedicated integrated circuit that can execute the computer program described above, such as a microcontroller, an ASIC, or an FPGA. In this case, the above computer program is pre-installed in a storage element provided in the dedicated integrated circuit. The storage element is an example for a computer-readable medium storing the computer program. The processor 122 of the prediction device 12 and the processor 32 of the model generation device 30 having the various functions described above may be each implemented by a combination of a general-purpose microprocessor and a dedicated integrated circuit.

The above embodiment is merely an example for facilitating understanding of the presently disclosed subject matter. Configurations according to the above embodiment can be appropriately changed and improved without departing from the gist of the presently disclosed subject matter.

In the above-described embodiment, the model generation device 30 generates the learned model 124 through supervised learning. However, the model generation device 30 may also generate the learned model 124 through unsupervised learning. In this case, the learning data LG can include load variation information indicating the variation over time of the load applied to the bed 20 when the subject is in the bed. When the variation over time in the load indicated by the detection signal DT received from the detection device 11 deviates from the learned variation over time in the load, the learned model 124 generated through this learning predicts that an event related to variation in fluid balance has occurred.

In the above embodiment, the model generation device 30 generates the learned model 124 through machine learning using a neural network. Alternatively, the learned model 124 may be generated through another machine learning algorithm. Examples of other machine learning algorithms include a decision tree, a random forest, a support vector machine, and the like.

The invention claimed is:

1. A fluid balance management system comprising:
a detection device configured to output a detection signal corresponding to a load applied to a bed in which a subject is present;
a prediction device configured to acquire load variation information indicating a variation over time of the load based on the detection signal, and predict an event that causes variation in fluid balance of the subject from the load variation information; and
an output device configured to output prediction information corresponding to a prediction result of the event.

2. The fluid balance management system according to claim 1, wherein
the output device is configured to output an image including an index corresponding to the prediction result together with the load variation information.

3. The fluid balance management system according to claim 1, wherein
the output device is configured to output body weight variation information indicating a body weight variation of the subject together with the prediction information.

4. The fluid balance management system according to claim 1, wherein
the prediction device is configured to predict the event by using a learned model obtained by machine learning.

5. The fluid balance management system according to claim 4, wherein
the learned model is configured to perform relearning in which record of correction of the prediction result is reflected in the prediction of the event.

6. A prediction device comprising:
an interface configured to receive load variation information indicating a variation over time of a load applied to a bed in which a subject is present, the variation over time being acquired based on a detection signal corresponding to the load; and
one or more processors configured to predict an event that causes variation in fluid balance of the subject from the load variation information, and output information corresponding to a prediction result of the event to an output device.

7. A non-transitory computer-readable storage medium storing a computer program executable by one or more processors mounted in a prediction device, wherein
when the computer program is executed, the prediction device:
receives load variation information indicating a variation over time of a load applied to a bed in which a subject is present, the variation over time being acquired based on a detection signal corresponding to the load;
predicts an event that causes variation in fluid balance of the subject from the load variation information; and
outputs information corresponding to a prediction result of the event to an output device.

8. A learned model generation device comprising:
an interface configured to receive, as learning data, a combination of load variation information indicating a variation over time of a load applied to a bed in which a subject is present, the variation over time being acquired based on a detection signal corresponding to the load, and event information indicating an event that causes variation in fluid balance of the subject associated with the variation over time; and
one or more processors configured to execute machine learning based on the learning data, thereby generating a learned model for predicting the event from the load variation information.

9. The learned model generation device according to claim 8, wherein
the machine learning is supervised learning.

10. A learned model generation method comprising:
receiving, as learning data, a combination of load variation information indicating a variation over time of a load applied to a bed in which a subject is present, the variation over time being acquired based on a detection signal corresponding to the load, and event information indicating an event that causes variation in fluid balance of the subject associated with the variation over time; and
executing machine learning based on the learning data, thereby generating a learned model for predicting the event from the load variation information.

11. A non-transitory computer-readable storage medium storing a computer program for performing the learned model generation method according to claim 10.

* * * * *